(12) United States Patent
Lee et al.

(10) Patent No.: US 11,607,172 B2
(45) Date of Patent: Mar. 21, 2023

(54) IMPEDANCE SENSOR FOR OPHTHALMIC DEVICE USING SHARED ANTENNA ELECTRODE

(71) Applicant: Verily Life Sciences LLC, South San Francisco, CA (US)

(72) Inventors: Shungneng Lee, Sunnyvale, CA (US); Tong Zhang, San Mateo, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 469 days.

(21) Appl. No.: 16/721,287

(22) Filed: Dec. 19, 2019

(65) Prior Publication Data

US 2020/0196949 A1 Jun. 25, 2020

Related U.S. Application Data

(60) Provisional application No. 62/784,205, filed on Dec. 21, 2018.

(51) Int. Cl.
*A61B 5/00* (2006.01)
*B29D 11/00* (2006.01)
(Continued)

(52) U.S. Cl.
CPC ...... *A61B 5/6821* (2013.01); *B29D 11/00817* (2013.01); *G02C 7/049* (2013.01); *G02C 7/083* (2013.01)

(58) Field of Classification Search
CPC ........ B29D 11/00817; B29D 11/00038; A61B 5/14507; A61B 5/6821; A61B 5/1486;
(Continued)

(56) References Cited

U.S. PATENT DOCUMENTS 7,169,106 B2 1/2007 Fleischman et al.
8,764,185 B1* 7/2014 Biederman ............ G02C 11/10
351/159.02
(Continued)

OTHER PUBLICATIONS

International Search Report and Written Opinion, dated Apr. 16, 2020, for corresponding International Patent Application No. PCT/US2019/067830, 13 pages.
(Continued)

*Primary Examiner* — Travis S Fissel
(74) *Attorney, Agent, or Firm* — Christensen O'Connor Johnson Kindness PLLC

(57) ABSTRACT

A contact lens system includes a shared antenna electrode, an accommodation actuator to provide variable optical power, and a controller coupled to the accommodation actuator and the shared antenna electrode. The controller including logic for arbitrating access to the shared antenna electrode between an impedance sensor and a communication circuit; selectively establishing an oscillator with the impedance sensor and the shared antenna electrode; correlating an oscillation condition of the oscillator to an accommodation setting; and adjusting the variable optical power of the accommodation actuator based upon the accommodation setting. An impedance across the shared antenna electrode varies based upon an amount an eyelid overlaps the contact lens system when the contact lens system is worn on an eye.

10 Claims, 8 Drawing Sheets

(51) Int. Cl.
*G02C 7/08* (2006.01)
*G02C 7/04* (2006.01)

(58) Field of Classification Search
CPC ... A61B 5/14532; A61B 5/145; A61B 5/1103; A61B 5/053; A61B 5/163; A61B 2560/0214; H01L 41/0471; H01L 41/113; G02C 7/04; G02C 7/049; G02C 7/083; G02C 11/10
USPC .... 351/159.02, 159.03, 159.39, 159.73, 178; 363/140
See application file for complete search history.

(56) References Cited

U.S. PATENT DOCUMENTS

| | | | |
|---|---|---|---|
| 8,857,983 B2 | 10/2014 | Pugh et al. | |
| 8,870,370 B1 | 10/2014 | Otis et al. | |
| 9,468,372 B2 | 10/2016 | Pugh et al. | |
| 9,825,364 B2 | 11/2017 | O'Driscoll | |
| 10,025,118 B1* | 7/2018 | Markus | B65B 7/16 |
| 2015/0245792 A1 | 3/2015 | Liu | |
| 2017/0042480 A1 | 2/2017 | Gandhi et al. | |
| 2017/0049395 A1 | 2/2017 | Cao | |
| 2017/0097524 A1 | 4/2017 | Honoré et al. | |
| 2018/0031867 A1 | 2/2018 | Lee et al. | |
| 2018/0154161 A1 | 6/2018 | Ackermann et al. | |
| 2018/0164607 A1 | 6/2018 | Wiser et al. | |
| 2018/0173013 A1 | 6/2018 | Robillotto et al. | |

OTHER PUBLICATIONS

Partial Supplementary European Search Report, dated Jul. 19, 2022, in European Patent Application No. 19901153.7-1126, 13 pages.
Extended Supplementary European Search Report, dated Oct. 20, 2022, in European Patent Application No. 19901153.7-1126, 11 pages.

* cited by examiner

IMPEDANCE SENSOR FOR OPHTHALMIC DEVICE USING SHARED ANTENNA ELECTRODE

CROSS-REFERENCE TO RELATED APPLICATIONS

This application claims the benefit of U.S. Application No. 62/784,205, filed on Dec. 21, 2018, the contents of which are incorporated herein by reference.

TECHNICAL FIELD

This disclosure relates generally to ophthalmic devices, and in particular but not exclusively, relates to accommodation control for accommodative contact lenses.

BACKGROUND INFORMATION

Accommodation is a process by which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that change the focal point of the elastic lens.

As an individual ages, increased stiffness of the eyes' lenses tend to decrease the effectiveness of the ciliary muscles in providing accommodation. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide (110 million in the United States alone) and that number is expected to substantially rise as the world's population ages.

Recent technologies have begun to provide for various devices that operate in or on a human eye to aid the visual focus of a user. For some types of these devices, an accommodating lens includes one or more elements and circuitry to apply an electrical signal to change a focusing/optical power of the one or more elements. Determining when to change such focusing power may be based on a direction of a gaze by a user of the optical device. As the capabilities of accommodation-capable optical devices continue to increase, there is expected to be an increased demand for such optical devices to provide accurate tracking of the direction of gaze by a user.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
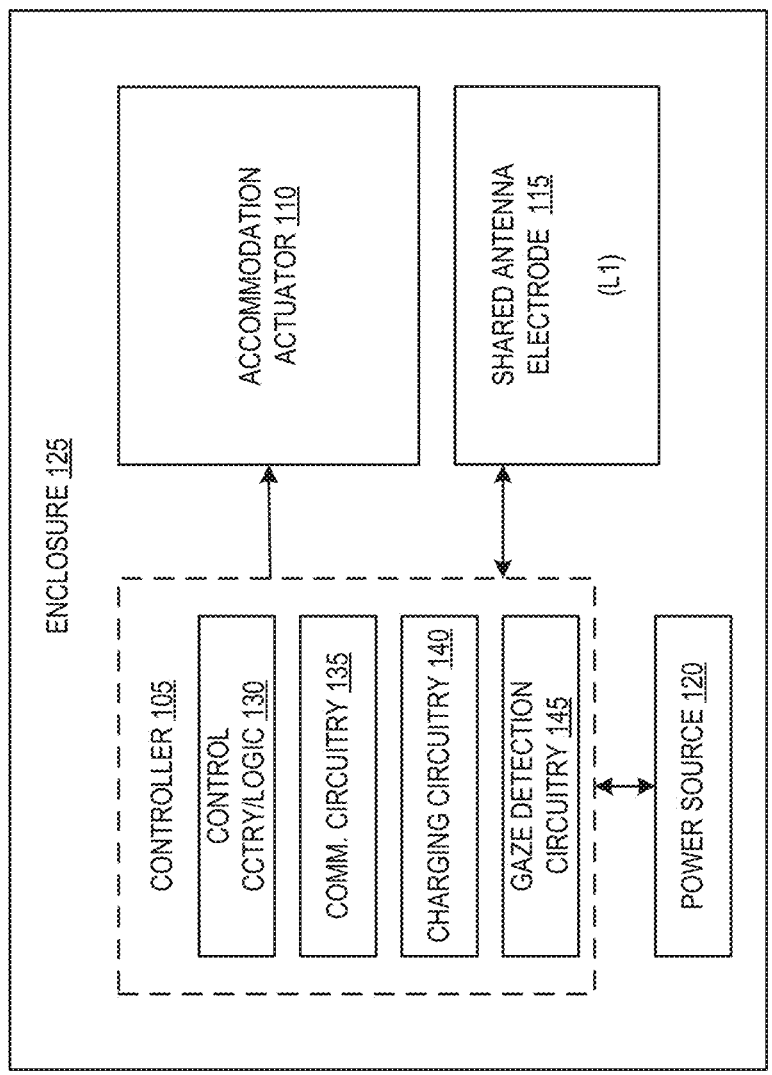
FIG. 1 illustrates a functional block diagram of an ophthalmic device including an antenna electrode that is shared across charging circuitry, communication circuitry, and gaze detection circuitry, in accordance with an embodiment of the disclosure.

Embodiments of an apparatus, system and method of operation for an ophthalmic device that shares a single antenna electrode between an impedance sensor for gaze/blink detection and other circuitry for communications and/or power charging are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The operation of an accommodating ophthalmic device (e.g., contact lens, intraocular lens, or other eyewear) requires a control mechanism for determining when and how much accommodation (optical power adjustment) is needed at a given moment. This accommodation control may be manual, fully automatic, or a hybrid of the two schemes. In some cases, the amount of accommodative optical power needed may be inferred from determining a user's direction of gaze. For example, if both user's eyes pivot inward or down, it may be inferred that the user is using their near-distance vision. Correspondingly, if the user's eyes are looking straight forward or up, it may be inferred that they are using their far-distance vision. A determination of an amount that a user's eyelids overlap the ophthalmic device may be used as a proxy for determining their gaze direction from which an accommodation setting may be correlated and used for feedback control to an accommodation actuator (i.e., variable power dynamic lens). The determination of eyelid overlap may also be used to identify blinks.

In some designs for eye-mountable devices (e.g., contact lens, IOL, etc.), the sensing of eyelid overlap is performed by photodetection to determine whether light is being prevented from reaching a photodiode that is disposed in an eye-mountable device (EMD). This use of light-based sensing has certain drawbacks—e.g., due to the wide dynamic range of ambient light in many typical environments. As an alternative to photodetector sensing, other EMD designs rely on a type of capacitive sensing, similar to that used in touchscreen technologies, to detect a capacitance of an eyelid. However, this type of capacitive sensing tends to have problems distinguishing a user's eyelid from the presence of a film of tear fluid (or "tear film") over the user's eye. It is believed that the conductivity of a tear film tends to block, or severely limit, the impact that a capacitance of a user's eyelid may otherwise have on dielectric and/or electric field properties of a fully-encapsulated capacitance sensor within an EMD. The tear film is believed to be a source of error in detecting eyelid capacitance.

Accordingly, embodiments described herein use an oscillator circuit that correlates an oscillation condition influenced by an impedance of an inductive antenna electrode to an amount of eyelid overlap, which in turn correlates to an accommodation setting for controlling an accommodation actuator. The impedance sensing used by the oscillator is capable of efficiently distinguishing between a tear film and eyelid overlap. Some embodiments detect a resistivity (and/or a change thereof) that is due to a combination of resistances each provided by a different respective one of a tear film and a user's eyelid.

Embodiments described herein have been refined to time-share the antenna electrode used by the impedance sensor with one or both of charging circuitry for wireless power harvesting and communication circuitry for RF wireless communications with devices external to the EMD. By intelligently and effectively arbitrating access to the shared antenna electrode, the use of multiple antenna electrodes is avoided, which reduces the rigid surface area of the EMD. A more flexible EMD provides greater comfort to the wearer. A timeshared single antenna electrode consumes less real estate to allow for a larger dynamic optic area. Less surface area dedicated to an antenna electrode, means less metallic area to reflect ambient light, thereby providing an improved cosmetic appearance. Finally, the intelligent arbitration and timesharing between charging circuitry, communication circuitry, and the gaze/blink detection circuitry (i.e., impedance sensor), enables each one of these components to more efficiently use the shared antenna electrode without negatively impacting, triggering, or loading the operation of the other components.

The impedance sensor incorporated into the gaze/blink detection circuitry described herein functions as an oscillator when coupled with the shared antenna electrode. The oscillator, including the shared antenna electrode and impedance sensor, commences oscillation based upon particular bias settings and an electromagnetic interaction between the shared antenna electrode and the tear film and a portion of the eyelid that overlaps the EMD (if at all). For example, a frequency of resonance by the oscillator may be based at least in part on inductive structures and capacitive structures of the ophthalmic device and such couplings to the structures of the eye. By evaluating operational characteristics of the oscillator, the various impedances of such inductive structures and capacitive structures may be accounted for, thus enabling detection of a resistive (real domain) component of impedance that is attributable to a tear film and any overlapping eyelid portion. Variation of such a resistive component may be proportional to an amount that the eyelid overlaps at least some portion of the sensor mechanism. The onset of an oscillation condition for the oscillator formed by the impedance sensor and the shared antenna electrode may, at a given time, be characterized by a minimum amount of current needed (at least at that time) to enable signal oscillation with that circuit. The required minimum amount of current may change over time with changes to the external environment adjoining the ophthalmic device—e.g., in proportion to a varying resistance that is provided by the tear film and any overlapping eyelid portion.

FIG. 1 is a functional block diagram of an ophthalmic device 100, such as a smart contact lens, including circuitry to detect whether at least a portion of ophthalmic device 100 is being overlapped by an eyelid of a user. Detection of this type of overlap (for brevity, referred to herein simply as "eyelid overlap") may be used, for example, for feedback control of an accommodation actuator.

The illustrated embodiment of ophthalmic device 100 includes a controller 105, an accommodation actuator 110, a shared electrode antenna 115, and a power source 120 all sealed within an enclosure 125. The illustrated embodiment of controller 105 includes control circuitry/logic 130, communication circuitry 135, charging circuitry 140, and gaze detection circuitry 145. In some embodiment, gaze detection circuitry 145 may be used (alternatively or additionally) to perform blink detection. It should be appreciated that FIG. 1 is a functional diagram and the illustrated components and circuitry may be implemented in hardware, software, or a combination of both. Furthermore, the physical components that implement the illustrated functions may be centralized as illustrated, or distributed. In one embodiment, controller 105 is implemented within a custom application specific integrated circuit (ASIC) that is mounted on an annular substrate within enclosure 125.

The enclosure material, represented by enclosure 125, may function as a light transmissive lensing material and may form, at least in part, a sealed enclosure in which is disposed circuitry of ophthalmic device 100. The dielectric enclosure material may be fabricated of a variety of materials compatible for direct contact with a human eye, such as a polymeric material, a hydrogel, PMMA, silicone based polymers (e.g., fluoro-silicon acrylate), or otherwise. Enclosure material 125 may be in the form of a round lens with a concave curvature configured to mount to a corneal surface of an eye. The electronics may be disposed upon a substrate embedded within the one or more enclosure materials near a periphery of ophthalmic device 100 to avoid interference with incident light received closer to the central region of the cornea.

Control circuitry/logic 105 represents miscellaneous components for orchestrating the operation of ophthalmic device 100. For example, control circuitry/logic 105 may be implemented with a microcontroller, on-board memory storing various software instructions, and may also include hardware logic configured to perform specific functions. Communication circuitry 135 may include RF electronics to receive, and in some embodiments also transmit, wireless data over shared antenna electrode 115. In one embodiment, communication circuitry 135 is a RF identification tag that uses backscatter communications. Charging circuitry 140 may include RF power rectification circuitry to harvest power from an RF carrier wave incident upon shared antenna electrode 115 and charge power source 120 (e.g., on-board battery, storage capacitor, etc.). Gaze detection circuitry 145 includes embodiments of the impedance sensor described herein, which selectively forms an oscillator with shared antenna electrode 115 to sense an amount of eyelid overlap and provide feedback control to accommodation actuator 110. Accommodation actuator 110 is a dynamic lens, such as a liquid crystal (LC) cell, a multi-layer LC diffractive lensing structure, an electrowetting lens, or otherwise.

Figure 2A:
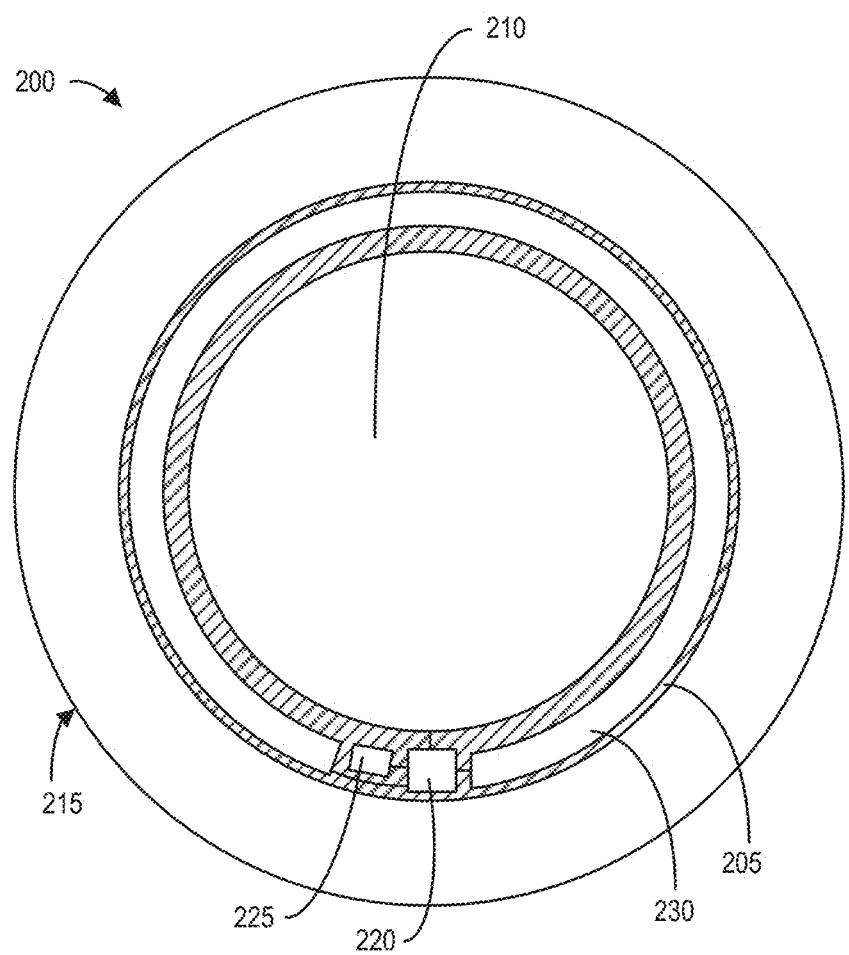
FIGS. 2A and 2B illustrate a plan view and perspective view of a contact lens system including a single ring-shaped antenna electrode, in accordance with an embodiment of the disclosure.
Figure 2B:
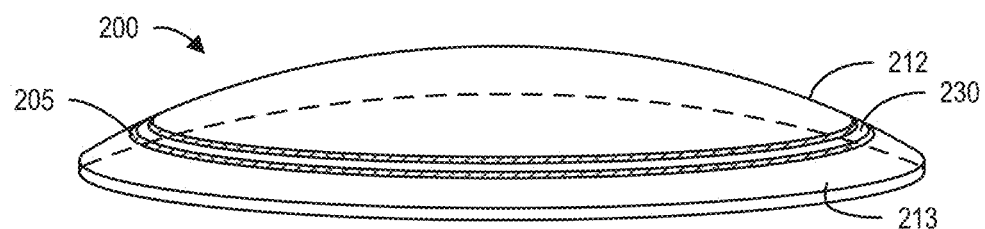

FIGS. 2A and 2B are illustrations of a contact lens system 200 including a dynamic diffractive liquid crystal lens, in addition to a gaze detection circuit that utilizes eyelid overlap sensing according to an embodiment of the disclosure. System 200 is one possible implementation of ophthalmic device 100 illustrated in FIG. 1. The illustrated embodiment of contact lens system 200 includes an annular substrate 205, a dynamic lens 210, an enclosure 215, a controller 220, a power source 225, and a ring-shaped antenna electrode 230. Enclosure 215 has a size and shape that mounts over the cornea of an eye. In the illustrated embodiment, enclosure 215 includes an anterior side 212 having a convex shape and a posterior side 213 having a concave shape. Of course, contact lens system 200 may assume other shapes and geometries including a piggyback configuration that attaches to a surface of an eye-mountable carrier substrate having an overall shape that resembles a conventional contact lens. Ring-shaped antenna electrode 230 is one possible implementation of shared antenna electrode 115. As illustrated, ring-shaped antenna electrode 230 encircles dynamic lens 210 and is coupled at either end to controller 220. In one embodiment, ring-shaped antenna electrode 230 is a single-ended antenna electrode structure in that one end is tied to a fixed potential (e.g., ground) while the other end is a tied to a shared terminal that is accessed by communication circuitry, charging circuitry, and an impedance sensor for gaze detection. The communication circuitry, charging circuitry, and gaze detection circuitry all timeshare ring-shaped antenna electrode 120, and in one embodiment, access between the communication circuitry and gaze detection circuitry is arbitrated.

Figure 3:
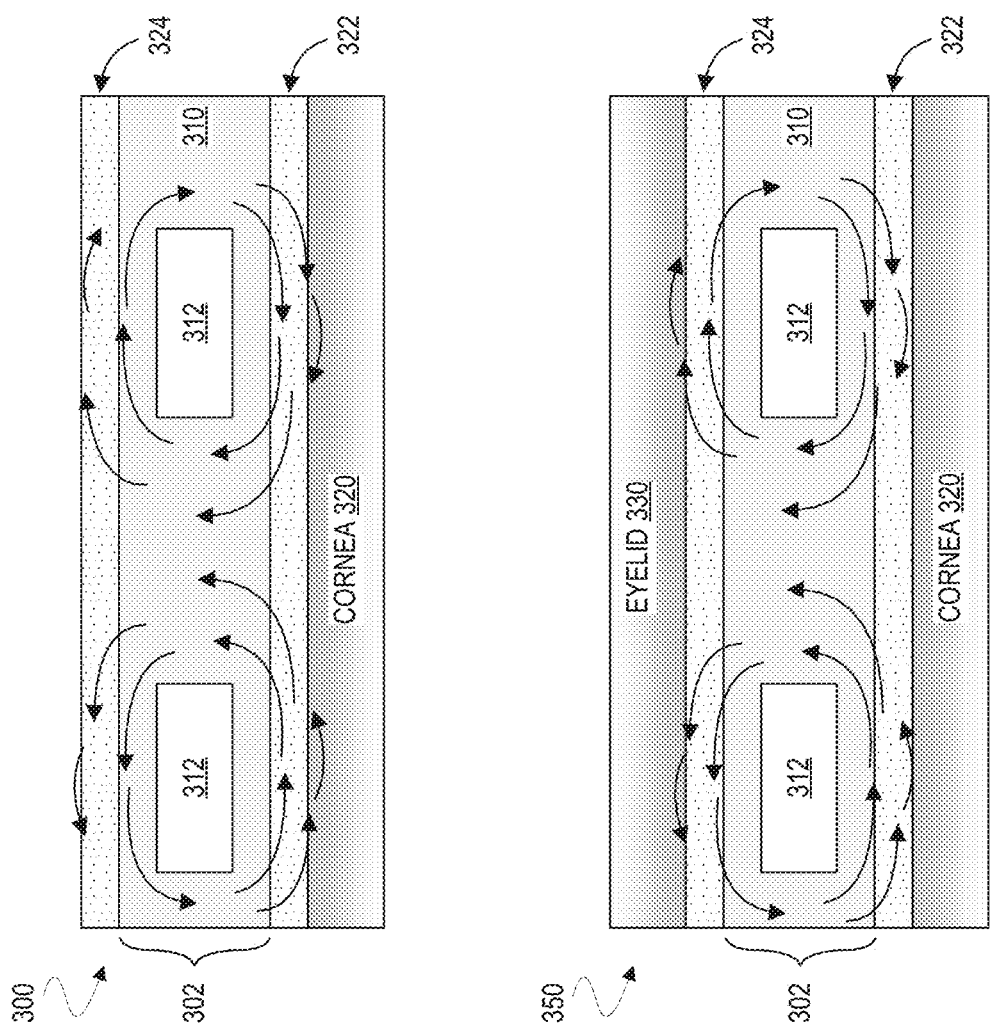
FIG. 3 illustrates cross-sectional views variously representing an ophthalmic device exposed or overlapped by an eyelid, in accordance with an embodiment of the disclosure.

FIG. 3 shows cross-sectional views—during respective states 300, 350—of a user's eye while that user is wearing an ophthalmic device 302 (e.g., ophthalmic device 100, contact lens system 200) according to an embodiment. Gaze detection circuitry including an impedance sensor may be fully encapsulated within an encapsulation material 310 of the ophthalmic device 302. Such encapsulation may aid in preventing moisture ingress during the operating lifetime of ophthalmic device 302. Operation of the impedance sensor, which forms an oscillator when connected with ring-shaped antenna electrode 312, may exploit the formation of a capacitive link which extends between a fully encapsulated electrode of the sensor circuit and the surface of a tear film. For brevity, this type of capacitive link is referred to herein as "lens capacitance."

A tear film may be conductive of a current that is induced by the oscillator. The effect of such conductivity on operational characteristics of the oscillator may change over time with the changing external environment—e.g., due to any additional conductance of a biological material (such as the eyelid) that comes in contact with the tear film. The extent to which an eyelid overlaps the sensor circuit may affect a resistivity of a current path that is in parallel with the tear film. In order to efficiently measure bio-conductance/bio-resistance of a tear film (in combination with that resulting from any eyelid overlap), some embodiments variously provide an inductive element L1 that, for example, is coupled in parallel with an in-series combination of lens capacitance Cp and two parallel resistances from the tear film RT and eyelid RE (see FIG. 4). During a resonance state of the oscillator, such an inductance element may cancel out or otherwise significantly offset an impedance provided with the lens capacitance Cp. Therefore, at the resonance state of the sensor circuit, the frequency of oscillation may be automatically determined as a resonance for a combination of the inductor L1 and the lens capacitance Cp, effectively exposing a total amount of resistance provided by the tear film RT and eyelid RE, if present, —e.g., where sensing of such resistance is not obscured by the impedance of the lens capacitance Cp. This resistance may directly correlate with, and be sensed by determining, a bias setting (e.g., a minimum amount of current) needed to startup oscillation of the oscillator. Accordingly, the impedance sensors described herein sense or measure the impedances RT and RE by determining a bias setting (e.g., setting of a current source) of an oscillator circuit at the onset of an oscillation condition.

An inductance element L1 may be formed, for example, with a ring-like configuration for the antenna electrode 312 that also contributes to lens capacitance. As mentioned, the impedance sensor of the gaze detection circuitry forms an oscillator circuit (e.g., Collpits oscillator structure) when selectively coupled to ring-shaped antenna electrode 312 that is configured to induce oscillation (resonance) with the antenna electrode that contributes to the lens capacitance. An amount of current required to achieve oscillation startup (e.g., onset of an oscillation condition) may be proportional to the amount of resistance across at least a portion of the tear film. Accordingly, a measurement of the startup current necessary to induce the oscillation condition is a proxy or measurement of the impedance across ring-shaped antenna electrode 312. At a time when an eyelid overlaps at least a portion of the ring-shaped antenna electrode 312, the resistance across an underlying portion of tear film may be relatively low, as compared to when there is relatively less (or no) eyelid overlap. A level of such bio-resistance may be measured in some embodiments by determining a threshold amount of current required to start oscillator of sensor circuitry.

During states 300 and 350, ophthalmic device 302 is disposed on a cornea 320 of the user's eye, wherein a tear film 322 extends between a cornea 320 of the eye and enclosure material 310 of ophthalmic device 302. Another tear film 324 may extend across an upper surface of enclosure material 310. State 300 represents a time when, as compared to state 350, an eye of the user is relatively more open. During state 350, an eyelid 330 of the user overlaps a surface area of enclosure material 310 that is larger than any area of enclosure material 310 that might be overlapped by eyelid 330 during state 300.

Figure 4:
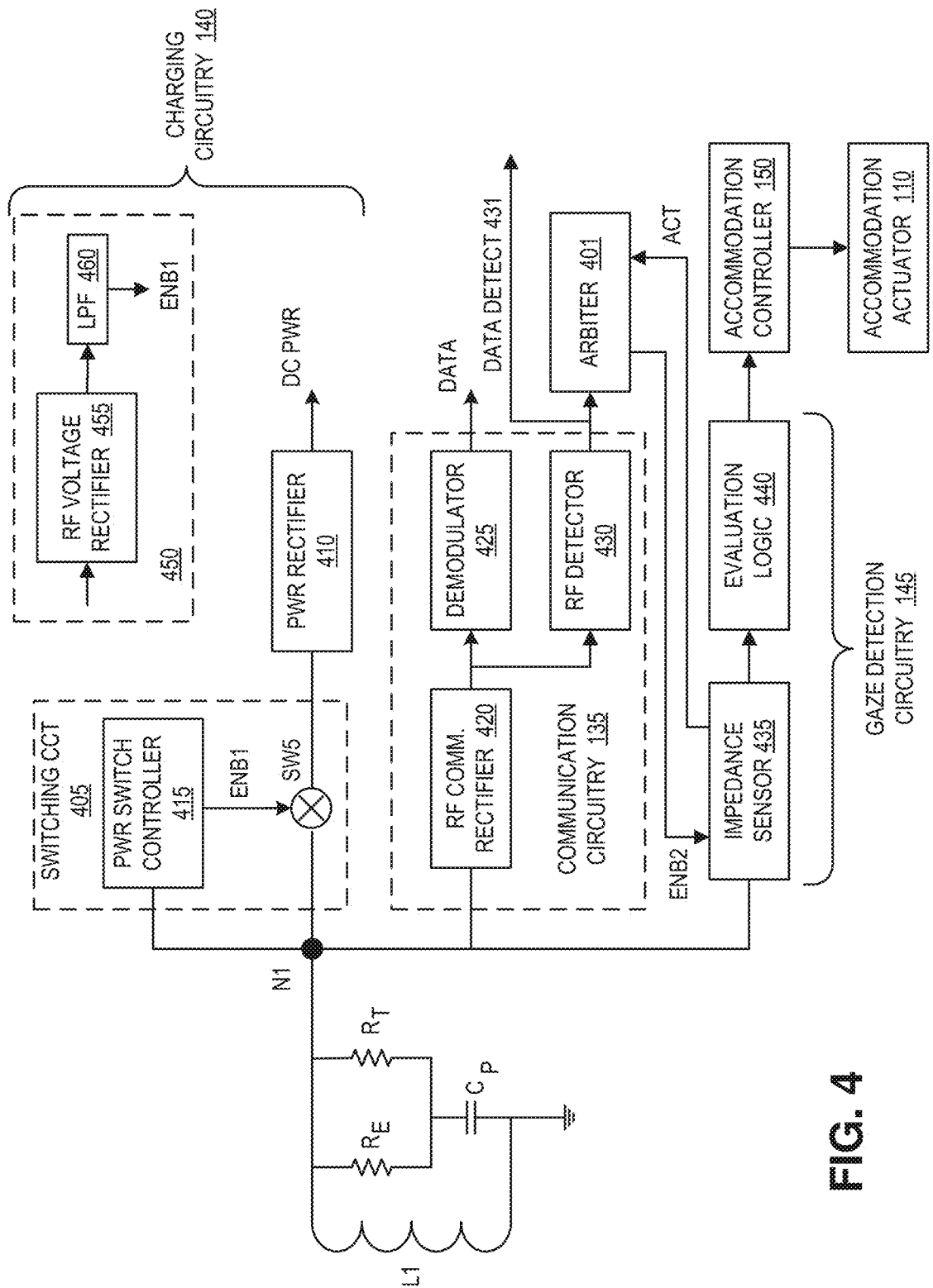
FIG. 4 is a hybrid circuit diagram and functional block diagram illustrating interrelations between the charging, communication, and gaze detection components of the ophthalmic device, in accordance with an embodiment of the disclosure.

FIG. 4 is a hybrid circuit diagram and functional block diagram illustrating the charging, communication, and gaze detection components of ophthalmic device 100, in accordance with an embodiment of the disclosure. Charging circuitry 140, communication circuitry 135, and gaze detection circuitry 145 all timeshare access to shared antenna electrode L1 through shared terminal N1. In one embodiment, the timeshared access is arbitrated by arbiter 401. The illustrated embodiment of charging circuitry 140 includes switching circuit 405 and RF power rectifier 410. The illustrated embodiment of switching circuit 405 includes a power switch controller 415 and a power switch SW5. The illustrated embodiment of communication circuitry 135 includes RF communication rectifier 420, demodulator 425, and RF detector 430. The illustrated embodiment of gaze detection circuitry 145 includes impedance sensor 435 and evaluation logic 440. Gaze detection circuitry 145 provides feedback control in the form of an accommodation setting to accommodation controller 150, which in turn drives accommodation actuator 110. Alternatively (or additionally), it should be appreciated that impedance sensor 435 may be used to perform blink detection. It should be appreciated that the illustrated components may be implemented in hardware circuits/logic, in software instructions/logic, or a combination of both hardware and software.

During operation power rectifier 410 serves to harvest power from a wireless signal, such as a radio frequency (RF) signal, to charge power source 120 and provide power to the other circuit components. Power rectifier 410 is coupled to shared antenna electrode L1 to harvest power from the wireless signal incident thereon. Switching circuit 405 is coupled to power rectifier 410 and shared terminal N1 to selectively couple a load of power rectifier 410 to shared antenna electrode L1 during power harvesting and in response to sensing a presence of the wireless signal on shared antenna electrode L1. Switching circuit 405 also decouples the load of power rectifier 410 when impedance sensor 435 is operating to measure the impedance of shared antenna electrode L1 so as to not unduly load or otherwise adversely affect the gaze detection circuitry.

In the illustrated embodiment, switching circuitry 405 includes a power switch SW5 coupled between shared terminal N1 and power rectifier 410 along with power switch controller 415 to control the switching operation of power switch SW5. Power switch controller 415 is coupled to shared terminal N1 to sense the presence or absence of an incident wireless signal for charging, and in turn controls power switch SW5 accordingly. In one embodiment, power switch SW5 is a transistor having its gate control terminal coupled to the output of power switch controller 415.

In one embodiment, power switch controller 415 operates as a low pass filter (LPF) voltage rectifier. When a voltage signal of sufficient amplitude is present on shared antenna electrode L1 due to an incident wireless signal, power switch controller 415 close circuits power switch SW5 when the time persistence of the wireless signal is sufficiently long. The amount of time persistence is physically set by the low pass filter corner frequency that is after the wireless signal rectifier (e.g., RF voltage rectifier 455). The target time persistence is determined by the wireless standard and required operating time of impedance sensor 435. Otherwise, power switch SW5 is open circuited to allow the other circuit components (e.g., impedance sensor 435) to access shared antenna electrode L1. Circuit 450 represents one possible implementation of power switch controller 415. As illustrated, the output of an RF voltage rectifier 455 is filtered by LPF 460, which generates an enable signal ENB1 for controlling a control terminal of power switch SW5. In one embodiment, the cutoff frequency of LPF 460 falls between a carrier frequency of the wireless signal used for wireless inductive charging via shared antenna electrode L1 and an oscillation frequency of impedance sensor 435 when operating for gaze detection. The low pass filtering prevents oscillations induced on shared antenna electrode L1 by impedance sensor 435 from triggering power switch SW5 and placing the load of power rectifier 410 on impedance sensor 435.

In yet another embodiment, power switch controller 415 may also be coupled to be responsive to arbiter 401, data detect signal 431, and/or active signal ACT output from impedance sensor 435. For example, power switch controller 415 may include logic to ensure that power switch SW5 is not closed circuited during an operational period of impedance sensor 435. In one embodiment, power switch controller 415 closes power switch SW5 when a wireless signal persists for longer than a preset time (e.g., 50 us).

Communication circuitry 420 is coupled to shared terminal N1 to receive wireless data via shared antenna electrode L1. RF communication rectifier 420 rectifies the analog signal and generates a baseband signal for demodulator 425. The baseband signal may be a simple form of amplitude-shift keying, such as on-off keying (OOK), which is then demodulated by modulator 425 to regenerate the data in digital form. RF detector 430 is coupled to receive the rectified signal and generate a data detect signal 431 indicating a presence of wireless data on shared antenna electrode L1. RF detector 430 may look for a pattern indicative of a rectified data signal.

Arbiter 401 is coupled to receive the data detect signal 431 from RF detector 430. If data detect signal 431 is high indicating the presence of RF data on shared antenna electrode L1, then arbiter 401 de-asserts enable signal ENB2 to impedance sensor 435 blocking its operation. On the other hand, if impedance sensor 435 is already operating, as indicated by an assertion of the active signal ACT from impedance sensor 435, then arbiter 401 will mask the assertion of the data detect signal 431 until impedance sensor 435 is complete and the active signal ACT is de-asserted. This masking prevents operation of impedance sensor 435 from being prematurely interrupted by arbiter 401 by new in-bound RF data.

Impedance sensor 435 is periodically enabled and coupled to shared terminal N1 in response to an assertion of the enable signal ENB2 from arbiter 401. Once impedance sensor 435 commences a gaze detection cycle, impedance sensor 435 asserts the active signal ACT to indicate to arbiter 401 that it is actively using shared antenna electrode L1. In one embodiment, impedance sensor 435 has a duty cycle of approximately 0.1%, or a period T1=5 to 10 ms and an evaluation period T2=5-10 us (see FIG. 6B).

Upon activating impedance sensor 435, it is coupled to shared antenna electrode L1 and forms an oscillator therewith. As previously mentioned, shared antenna electrode L1 has an impedance that varies based upon an amount an eyelid overlaps shared antenna electrode L1, which in turn is related to the user's gaze direction. This impedance forms part of an RLC oscillator circuit with impedance sensors 435, and as such, the user's gaze direction influences an oscillation condition of the oscillator. During each evaluation period, impedance sensor 435 iteratively resets the oscillator, re-biases the oscillator, perturbs the oscillator, and then monitors for the onset of an oscillation condition. The bias level of the oscillator at the point where the oscillator commences oscillation when perturbed is correlated by evaluation logic 440 to a gaze direction, and by extension, to an accommodation setting. A binary search algorithm may be executed to quickly identify the bias conditions that result in the onset of an oscillation condition. In one embodiment, evaluation logic 440 uses a lookup table to correlate bias settings to an accommodation setting. The lookup table may be pre-calibrated, calibrated per user, or even periodically calibrated by a given user. The accommodation setting is then used by accommodation controller 150 to adjust the optical power of accommodation actuator 110.

Figure 5:
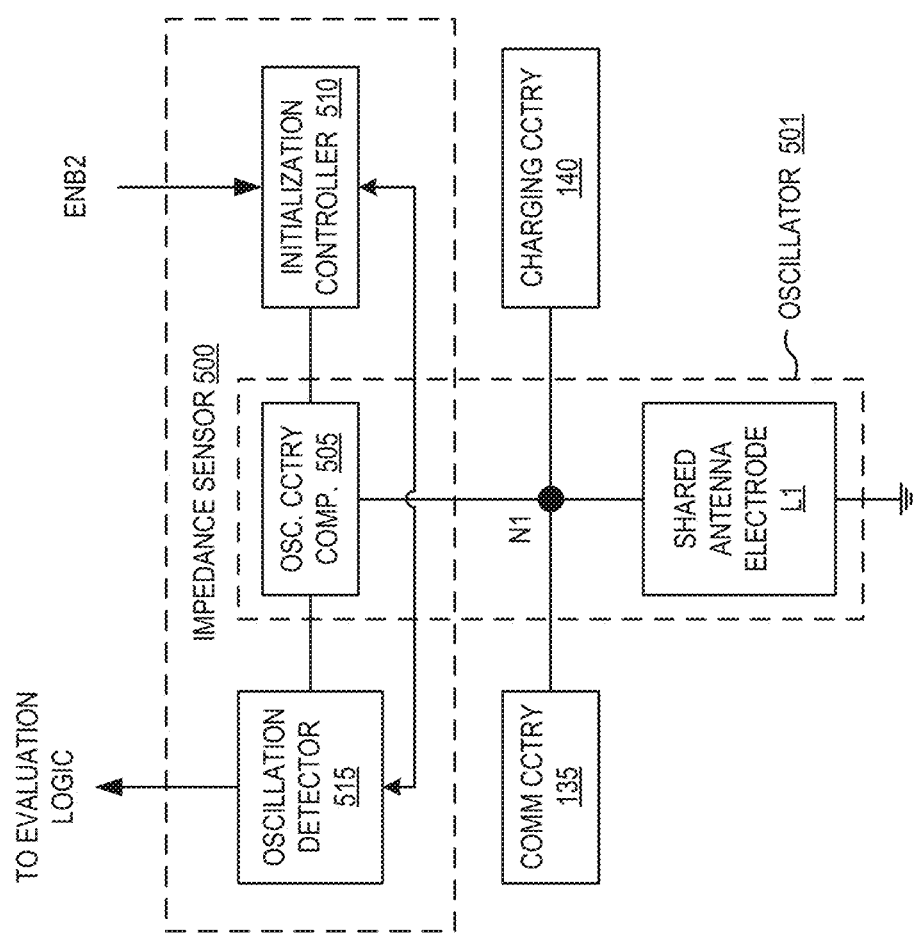
FIG. 5 is a functional block diagram illustrating functional components of the impedance sensor within the gaze detection circuitry, in accordance with an embodiment of the disclosure.

FIG. 5 is a functional block diagram illustrating functional components of an impedance sensor 500, in accordance with an embodiment of the disclosure. Impedance sensor 500 is one possible implementation of impedance sensor 435. The illustrated embodiment of impedance senor 500 includes oscillator circuitry components 505, an initialization controller 510, and an oscillation detector 515.

In response to the enable signal ENB2 being asserted by arbiter 401, initialization controller 510 configures oscillator circuitry components 505 to establish an oscillator 501 with shared antenna electrode L1. While ENB2 is asserted, initialization controller 510 iteratively resets oscillator 501, re-biases one or more oscillator circuitry components 505, and perturbs oscillator 501. Concurrently, oscillation detector 515 monitors oscillator 501 for the onset of an oscillation condition. For example, oscillation detector 515 may be coupled to monitor shared terminal N1 for a characteristic oscillation signal (e.g., repetition of a specified amplitude and/or frequency). Accordingly, in one embodiment, oscillation detector 515 may include an amplitude and/or frequency comparator along with a counter that is reset with each initialization iteration by initialization controller 510. The bias level of the oscillator circuitry components 505 at the point where the oscillator commences oscillation when perturbed is then provided to evaluation logic 440 for correlation to an accommodation setting. Initialization controller 510 may execute a binary search algorithm to quickly and efficiently identify the onset of the oscillation condition.

Oscillation detector 515 may couple to any number of circuit nodes within oscillator circuitry components 505 (or 600) to monitor for an oscillation condition. In one embodiment, oscillation detector 515 is coupled to shared node N1 (see FIG. 6A), which may also be considered an interconnecting node of oscillator circuitry components 505. The double arrowed connection illustrated in FIG. 5 connecting oscillation detector 515 to initialization controller 510 symbolizes that these two components may be coupled to communication with each other. For example, oscillation detector 515 may inform initialization controller 510 that a given iteration of biasing current source CS1 did or didn't trigger an oscillation condition. Correspondingly, initialization controller 510 may be coupled to oscillation detector 515 to enable or disable its operation.

Figure 6A:
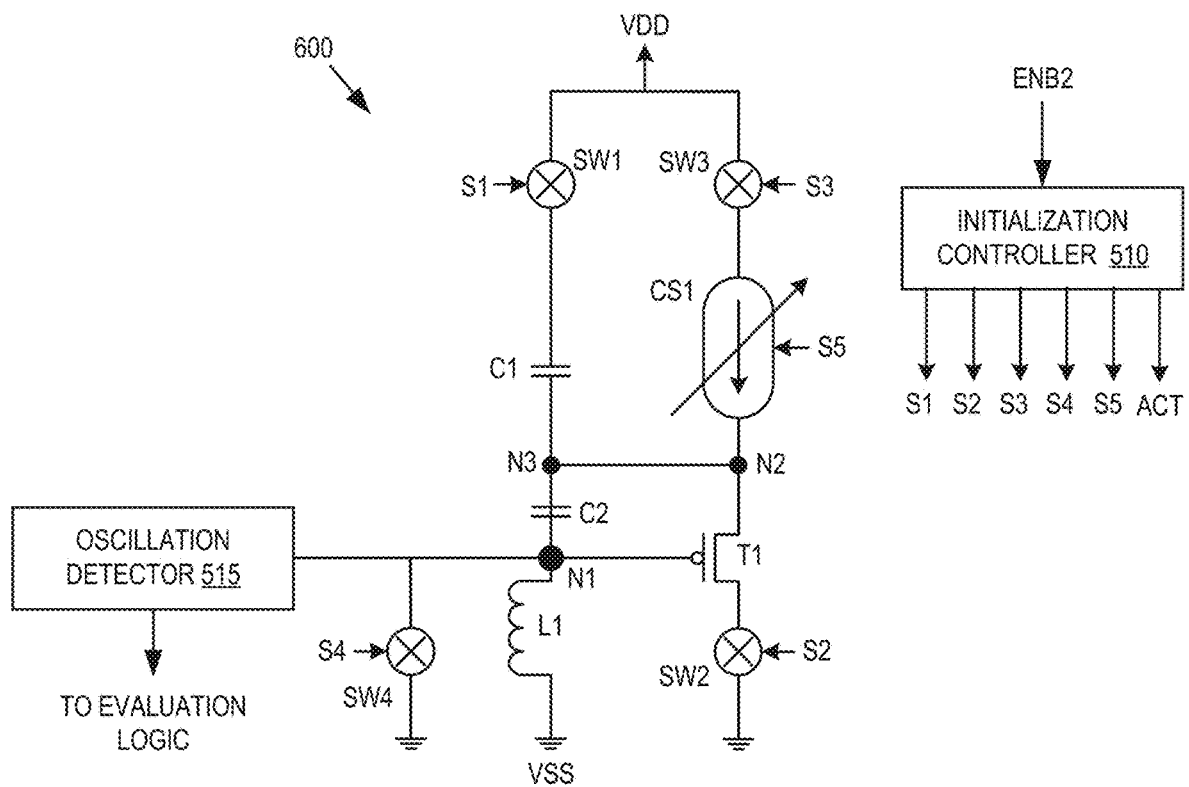
FIG. 6A is a circuit diagram illustrating the oscillator circuitry components for establishing an oscillator with a shared antenna electrode, in accordance with an embodiment of the disclosure.

FIG. 6A is a circuit diagram illustrating oscillator circuitry components 600 that couple with shared antenna electrode L1 to form an oscillator (e.g., oscillator 501), in accordance with an embodiment of the disclosure. Oscillator circuitry components 600 are one possible implementation of oscillator circuitry components 505 in FIG. 5.

The illustrated embodiment of oscillator circuitry components 600 includes current source CS1, transistor T1, capacitors C1 and C2 along with switches SW1, SW2, SW3, and SW4. Transistor T1 has a channel coupled in series with current source CS1 between high voltage rail VDD and low voltage rail VSS (e.g., ground). The pair of capacitors C1 and C2 are coupled in series between VDD and shared terminal N1. A gate of transistor T1 is coupled to shared terminal N1. Circuit node N2 between transistor T1 and current source CS1 is coupled to circuit node N3 between capacitors C1 and C2. Switch SW1 is coupled in series between VDD and capacitor C1. Switch SW2 is coupled in series between VSS and the channel of transistor T1. Switch SW3 is coupled in series between VDD and current source CS1.

When switches SW1, SW2, and SW3 are closed, the oscillator circuitry components 600 establish an RLC oscillator (e.g., oscillator 501) with shared antenna electrode L1. When switches SW1, SW2, SW3, and SW4 are open, the oscillator is disabled and shared antenna electrode L1 is available for use by communication circuitry 135 or charging circuitry 140 without undue interference from impedance sensor 435. Switch SW4 is a reset switch that operates to reset the voltage at shared terminal N1 between each iteration of initializing (e.g., adjusting the startup current output from current source CS1 via control signal S5) and perturbing oscillator 501 during operation of impedance sensor 435 for gaze detection.

Switches SW1, SW2, SW3, and SW4 may be implemented as transistors (e.g., NMOS transistors) while transistor T1 may be implemented as a PMOS transistor. In the illustrated embodiment, current source SC1 is a variable current source that varies its output current in response to a control signal S5. In the illustrated embodiment, switches SW1, SW2, SW3, and SW4 along with current source CS1 operate under the influence of control signals S1-S5 output from initialization controller 510.

In the illustrated embodiment, oscillator circuitry components 600 form a single-ended oscillator, such as a Colpitts oscillator, with shared antenna electrode L1, which represents the inductive element of the RLC oscillator. The resistive elements of the RLC oscillator arise from RE and RT (only illustrated in FIG. 4). Although FIG. 6A illustrates oscillator circuitry components 600 as forming a Colpitts oscillator, it should be appreciated that other oscillator configurations may be implemented. For example, oscillator circuitry components 600 may form a Harley oscillator, an Armstrong oscillator, or other variations of single-ended oscillators.

In the illustrated embodiment, the oscillator formed by oscillator circuitry components 600 and shared antenna electrode L1 is a single-end oscillator (as opposed to a differential oscillator) and shared antenna electrode L1 is configured as a single-ended inductive element having its opposite terminal tied to a fixed potential (e.g., grounded) while its single ended output terminal (i.e., shared terminal N1) is coupled to the single input of oscillator 501. It should be appreciated that other configurations than just a single-ended oscillator may also be implemented.

Oscillation detector 515 is coupled to oscillator 501 to monitor oscillator 501 for the onset of an oscillation condition. In the illustrated embodiment, oscillation detector 515 is coupled to shared terminal N1, although it may be coupled to other circuit nodes that express an oscillating signal when oscillator 501 is operating in an oscillation regime.

Figure 6B:
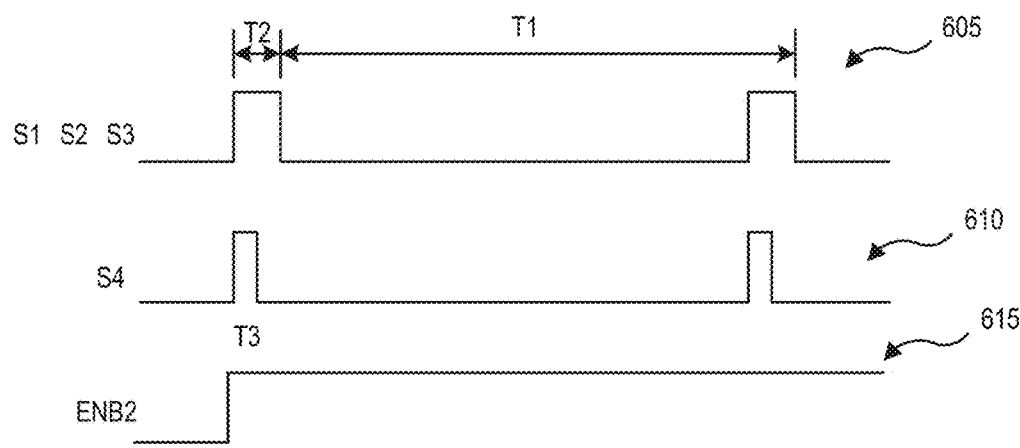
FIG. 6B is a timing diagram illustrating timing operation of an oscillator established between an impedance sensor and a shared antenna electrode, in accordance with an embodiment of the disclosure.

FIG. 6B illustrates a timing diagram for the operation of the oscillator circuit illustrated in FIG. 6A. Trace 605 illustrates the operation of control signals S1, S2, and S3, which have an evaluation period T2 of approximately 5-10 us and a duty cycle of approximately 0.1% (e.g., T1=5 to 10 ms). Trace 610 illustrates control signal S4 used to reset shared terminal N1. Control signal S4 is asserted at the beginning of each evaluation period T2 for a portion (e.g., T3=0.5*T2) of the evaluation time. T3 may be thought of as a reset period. Of course, T1, T2, and T3 may be implemented with other durations and duty cycles. Trace 615 illustrates that initialization controller 510 activates oscillator 501 by closing switches SW1, SW2, and SW3 in response to arbiter asserting the enable signal ENB2.

Figure 7A:
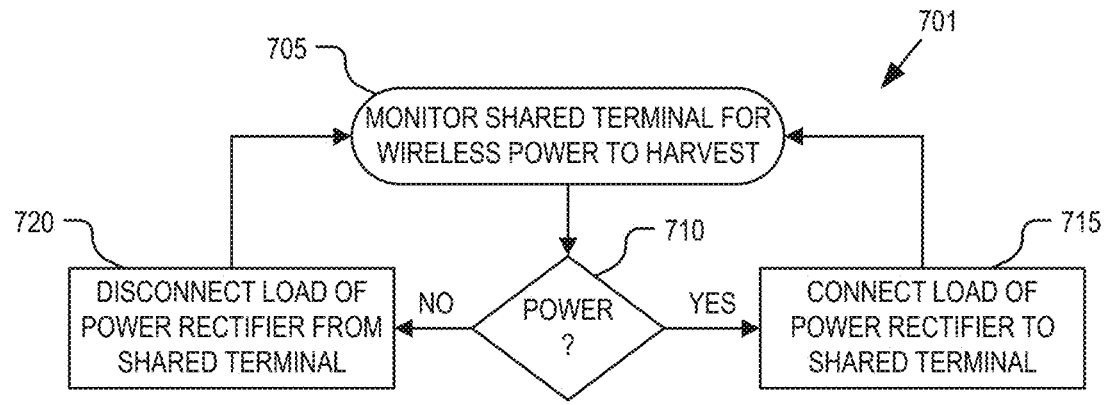
FIG. 7A is a flow chart illustrating a process of operation of a power switch controller for coupling a load of a power rectifier to a shared antenna electrode, in accordance with an embodiment of the disclosure.

FIG. 7A is a flow chart illustrating a process 701 for operation of power switch controller 415 illustrated in FIG. 4, in accordance with an embodiment of the disclosure. The order in which some or all of the process blocks appear in process 701 should not be deemed limiting. Rather, one of ordinary skill in the art having the benefit of the present disclosure will understand that some of the process blocks may be executed in a variety of orders not illustrated, or even in parallel.

As mentioned above, power switch controller 415 operates to selectively couple and decouple the load of power rectifier 410 to/from shared terminal N1 and shared antenna electrode L1. In a process block 705, power switch controller 415 monitors shared terminal N1 for a wireless signal having power to harvest. If a wireless signal having power to harvest is determined to be present on shared antenna electrode L1 (decision block 710), then enable signal ENB1 is asserted and shared antenna electrode L1 is loaded by power rectifier 410 (process block 715). If a wireless signal having power to harvest is determined not present on shared antenna electrode L1 (decision block 710), then enable signal ENB1 is de-asserted and the load of power rectifier 410 is isolated from shared antenna electrode L1. In one embodiment, power switch controller 415 includes a voltage rectifier and low pass filter that permits the lower carrier frequency of the wireless power signal to pass through the low pass filter after rectification to enable switch SW5. In contrast, the oscillation frequency of impedance sensor 435 (and oscillator 501) are too high to pass through LPF 460. Accordingly, power switch controller 415 operates to ensure the higher frequency operation of impedance sensor 435 does not trigger power harvesting thereby loading impedance sensor 435 with power rectifier 410. In an embodiment implemented with RF voltage rectifier 455, the rectification circuitry of RF voltage rectifier 455 may be voltage matched such that the amplitude of oscillations on shared antenna electrode L1 due to impedance sensor 435 are too small for threshold voltage rectification by RF voltage rectifier 455 and thus will not active switch SW5. Other control logic may be used to implement the above described functionality of power switch controller 415.

Figure 7B:
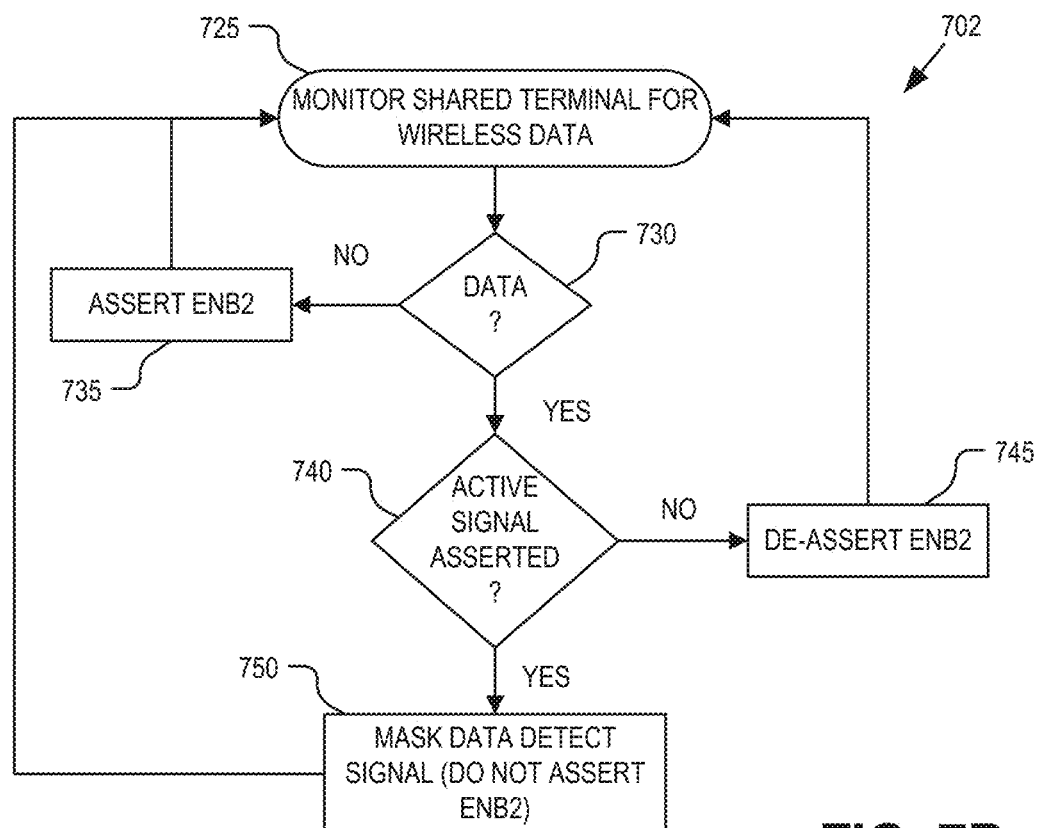
FIG. 7B is a flow chart illustrating a process of operation of an arbiter for timesharing access to a shared antenna electrode, in accordance with an embodiment of the disclosure.

FIG. 7B is a flow chart illustrating a process 702 for arbitrating access to shared antenna electrode L1, in accordance with an embodiment of the disclosure. The order in which some or all of the process blocks appear in process 702 should not be deemed limiting. Rather, one of ordinary skill in the art having the benefit of the present disclosure will understand that some of the process blocks may be executed in a variety of orders not illustrated, or even in parallel.

In a process block 725, RF communication rectifier 420 and RF detector 430 monitor shared terminal N1 for the presence of wireless data on shared antenna electrode L1. If data is determined not present (decision block 730), then data detect signal 431 is de-asserted and arbiter 401 in turn asserts the enable signal ENB2 to impedance sensor 435 indicating that impedance sensor 435 is granted access to shared antenna electrode L1 for gaze detection. However, if wireless data is determined present (decision block 730), then data detect signal 431 is asserted and arbiter 401 reads the active signal ACT from impedance sensor 435 to see if impedance sensor 435 is currently using shared antenna electrode L1. If the active signal ACT is not currently asserted by impedance sensor 435 (decision block 740), then in response, arbiter 401 de-asserts the enable signal ENB2 to impedance sensor 435, thereby blocking impedance sensor 435 from operating on shared antenna electrode L1 while wireless data is received. However, if the active signal ACT is currently asserted (decision block 740) indicating that impedance sensor 435 is currently using shared antenna electrode L1, then arbiter 401 masks data detect signal 431 to permit impedance sensor 435 to complete its gaze detection operation, thereby temporarily delaying de-assertion of the enable signal ENB2 until the active signal ACT is de-asserted and impedance sensor 435 has indicated its completion.

Figure 7C:
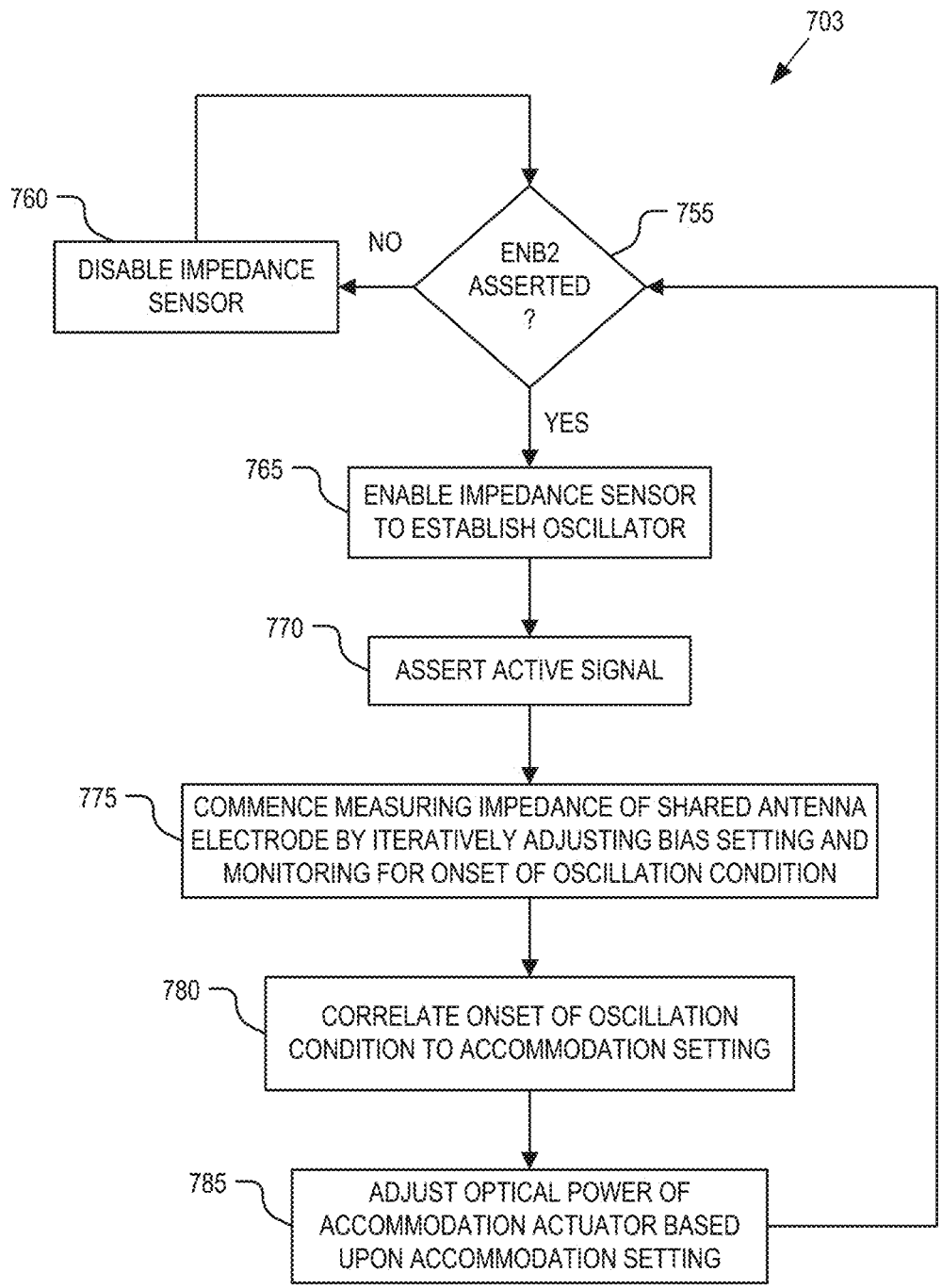
FIG. 7C is a flow chart illustrating a process of operation of gaze detection circuitry to provide auto-accommodation feedback control to an accommodation actuator, in accordance with an embodiment of the disclosure.

FIG. 7C is a flow chart illustrating a process 703 for operation of gaze detection circuitry 145 to provide accommodation feedback control to accommodation actuator 110, in accordance with an embodiment of the disclosure. The order in which some or all of the process blocks appear in process 703 should not be deemed limiting. Rather, one of ordinary skill in the art having the benefit of the present disclosure will understand that some of the process blocks may be executed in a variety of orders not illustrated, or even in parallel.

In a decision block 755, initialization controller 510 monitors the enable signal ENB2 from arbiter 401. If the ENB2 is unasserted, then arbiter 401 has not granted impedance sensor 435 access to shared antenna electrode L1 and therefore impedance sensor 435 remains disabled. In one embodiment, disabling impedance sensor 435 includes open circuiting switches SW1, SW2, SW3, and SW4 to disable oscillator 501. However, if ENB2 is asserted by arbiter 401, then process 703 continues to a process block 765.

In process block 765, impedance sensor 435 (or 500) is enabled and oscillator 501 is established between oscillation circuitry components 505 and shared antenna electrode L1. In one embodiment, establishing oscillator 501 includes close circuiting switches SW1, SW2, and SW3. Initially, switch SW4 is close circuited to reset the voltage at shared terminal N1 to a default voltage (e.g., VSS or ground). In response to accessing shared antenna electrode L1, initialization controller 510 asserts the active signal ACT to indicate to arbiter 401 that impedance sensor 435 is actively using shared terminal N1 and shared antenna electrode L1 for gaze detection (process block 770).

In a process block 775, impedance sensor 435 commences measuring the impedance of shared antenna electrode L1 by iteratively adjusting one or more bias settings (e.g., startup current of current source CS1), perturbing oscillator 501, and monitoring for the onset of an oscillation condition. Between iterations, initialization controller 510 resets the voltage at shared terminal N1 by close circuiting reset switch SW4. Oscillator 501 is perturbed after readjusting the bias setting of current source CS1. The perturbation is instigated by opening switch SW4 after the reset period T3 expires. Oscillation self-starts due to inherent circuit noise and the action of releasing switch SW4 (that will have some parasitic capacitance to "kick" oscillator 501), as well as having a sufficient bias setting for current source CS1. Oscillation detector 515 monitors a circuit node (e.g., shared terminal N1) within oscillator 501 for a characteristic oscillation signal (e.g., repetition of a specified amplitude and/or frequency). If oscillation does not occur, then the next iteration is commenced by resetting the voltage at shared terminal N1 with switch SW4, adjusting the bias setting of current source CS1, and perturbing oscillator 501 again. This iterative process continues until the onset of the oscillation condition is detected by oscillation detector 515. In one embodiment, initialization controller 510 uses a binary search algorithm to quickly identify the bias setting for current source CS1 that just results in the onset of the oscillation condition.

In a process block 780, evaluation logic 440 correlates the onset of the oscillation condition to an accommodation setting. This correlation may reference a lookup table, be the product of a machine learning algorithm, or otherwise. In one embodiment, the lookup table is calibrated by asking the user to follow a series of gaze calibration instructions (e.g., look up, look down, read a book, etc.) while impedance sensor 435 measures the impedance of shared antenna electrode L1. Finally, in a process block 785, accommodation controller 150 uses the selected accommodation setting output from evaluation logic 440 to manipulate the optical power of accommodation actuator 110. In one embodiment, accommodation actuator 110 is a dynamic LC lens, which changes its optical power in response to changes in a bias voltage applied across the LC material of the dynamic LC lens.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device, comprising:
   an enclosure shaped for mounting in or on an eye;
   an antenna electrode disposed within the enclosure, the antenna electrode having a shared terminal;
   an impedance sensor coupled to the shared terminal of the antenna electrode, the impedance sensor forming an oscillator with the antenna electrode, wherein the antenna electrode has an impedance that varies based upon an amount an eyelid overlaps the enclosure when the ophthalmic device is mounted in or on the eye and wherein the impedance influences an oscillation condition of the oscillator;
   a power rectifier coupled to the antenna electrode to harvest power from a wireless signal incident upon the antenna electrode; and
   a switching circuit coupled to the power rectifier and the shared terminal to selectively couple a load of the power rectifier to the antenna electrode to allow the power rectifier to harvest the power from the wireless signal and to decouple the load of the power rectifier while the impedance sensor is operating to measure the impedance of the antenna electrode.

2. The ophthalmic device of claim 1, wherein the switching circuit comprises:
   a power switch coupled between the shared terminal and the power rectifier; and
   a power switch controller coupled to the shared terminal and to a control terminal of the power switch, the power switch controller configured to close circuit the power switch when detecting the wireless signal via the antenna electrode and open circuit the power switch in an absence of detecting the wireless signal via the antenna electrode.

3. The ophthalmic device of claim 2, wherein the power switch controller comprises:
   a voltage rectifier having an input coupled to the shared terminal; and
   a low pass filter (LPF) coupled between an output of the voltage rectifier and the control terminal of the power switch, wherein a cutoff frequency of the LPF falls between a carrier frequency of the wireless signal and an oscillation frequency of the impedance sensor.

4. The ophthalmic device of claim 1, further comprising:
   communication circuitry coupled to the shared terminal of the antenna electrode, the communication circuitry configured to receive wireless data via the antenna electrode; and
   an arbiter coupled to the communication circuitry and to the impedance sensor to arbitrate timesharing of the antenna electrode between the communication circuitry and the impedance sensor, wherein the impedance sensor is enabled in response to an enable signal from the arbiter.

5. The ophthalmic device of claim 4, wherein the communication circuitry is configured to assert a data detect signal in response to detecting the wireless data on the antenna electrode, wherein the impedance sensor is configured to assert an active signal when actively using the antenna electrode, and wherein the arbiter includes logic that activates the enable signal while the data detect signal is de-asserted and masks the data detect signal while the active signal from the impedance sensor is asserted.

6. The ophthalmic device of claim 4, wherein the impedance sensor includes oscillator circuitry components interconnected with switches, and wherein the oscillator circuit components are arranged to form a Colpitts oscillator with the antenna electrode when the switches are close circuited in response to the enable signal from the arbiter and the switches are further arranged to disable the Colpitts oscillator when open circuited.

7. The ophthalmic device of claim 6, wherein the oscillator circuitry components comprise:
   a transistor having a channel coupled in series with a current source between first and second voltage rails;
   a pair of capacitors coupled in series between the first voltage rail and the shared terminal of the antenna electrode, wherein a gate of the transistor is coupled to the shared terminal and a first circuit node between the transistor and the current source is coupled to a second circuit node between the pair of capacitors, wherein the switches include a first switch coupled between the first voltage rail and the pair of capacitors, a second switch coupled between the second voltage rail and the transistor, and a third switch coupled between the first voltage rail and the current source.

8. The ophthalmic device of claim 6, wherein the impedance sensor further comprises:

an oscillation detector coupled to the shared terminal to monitor the oscillator for an onset of the oscillation condition;

a fourth switch coupled to the shared terminal to selectively reset a voltage of the shared terminal; and an initialization controller coupled to the switches including the fourth switch to selectively open and close the switches in response to the enable signal.

9. The ophthalmic device of claim 1, wherein the oscillator and the antenna electrode are single ended and coupled together at the shared terminal.

10. The ophthalmic device of claim 1, further comprising:

evaluation logic coupled to the impedance sensor to correlate an occurrence of the oscillation condition with an accommodation setting;

an accommodation actuator disposed within a central region of the enclosure to provide variable optical power, wherein the antenna electrode at least partially encircles the accommodation actuator; and an accommodation controller coupled to the accommodation actuator to control the variable optical power in response to the accommodation setting determined by the evaluation logic.

* * * * *